United States Patent
Williams et al.

(10) Patent No.: US 7,326,823 B2
(45) Date of Patent: Feb. 5, 2008

(54) AROMATIC COMPOUND RECOVERY

(75) Inventors: Solon B. Williams, Kingwood, TX (US); Reynaldo E. Vera, Alvin, TX (US); Robert W. Whitmire, Alvin, TX (US); Paul A. Barnard, League City, TX (US); Brian J. Narowski, Friendswood, TX (US)

(73) Assignee: Equistar Chemicals, LP, Houston, TX (US)

( * ) Notice: Subject to any disclaimer, the term of this patent is extended or adjusted under 35 U.S.C. 154(b) by 584 days.

(21) Appl. No.: 11/044,128

(22) Filed: Jan. 27, 2005

(65) Prior Publication Data

US 2006/0167328 A1   Jul. 27, 2006

(51) Int. Cl.
*C07C 7/10* (2006.01)
*B01D 3/40* (2006.01)
*B01D 3/42* (2006.01)

(52) U.S. Cl. .................. 585/956; 585/804; 585/833; 203/3; 203/50

(58) Field of Classification Search ............. 585/800, 585/802, 804, 805, 833, 864, 956; 203/1, 203/3, 50, 57
See application file for complete search history.

(56) References Cited

U.S. PATENT DOCUMENTS

| | | | |
|---|---|---|---|
| 2,773,918 A | 12/1956 | Stephens | 260/674 |
| 3,361,664 A | 1/1968 | Broughton et al. | 208/313 |

FOREIGN PATENT DOCUMENTS

WO    WO 03/022390 A2 *   3/2003

* cited by examiner

*Primary Examiner*—Glenn Caldarola
*Assistant Examiner*—Randy Boyer
(74) *Attorney, Agent, or Firm*—Roderick W. MacDonald

(57) ABSTRACT

A method for the solvent extraction recovery of an aromatic wherein an aromatic extract is formed that contains the aromatic and non-aromatics that are both lighter than and heavier than the aromatic, analyzing at least two separate groups of lighter and heavier non-aromatics in the extract, determining from the analyses the distribution of lighter and heavier non-aromatics present and whether the aromatic product that will be recovered from the process will be too far from its predetermined maximum non-aromatic content specification, and making process changes that will cause the process to produce the aromatic product with a non-aromatic content that is closer to its predetermined maximum non-aromatic content specification.

8 Claims, 2 Drawing Sheets

AROMATIC COMPOUND RECOVERY

BACKGROUND OF THE INVENTION

1. Field of the Invention

This invention relates to the recovery of one or more aromatic hydrocarbon compounds (aromatic or aromatics) from a mixture of such aromatics and one or more non-aromatic hydrocarbon compounds (non-aromatic or non-aromatics) using solvent extraction, extractive distillation, and reboiled stripping techniques.

2. Description of the Prior Art

Although, for the sake of clarity and brevity, this invention will sometimes be described hereinafter in respect of the recovery of benzene alone, it is to be understood that this invention is applicable as well to the recovery of aromatic products in general such as toluene, xylenes (ortho, meta, and/or para isomers), ethyl benzene, and the like, individually or in any combination or mixture of two or more thereof.

Heretofore, the recovery of one or more aromatic products from a feed composed of a mixture of at least one aromatic and at least one non-aromatic has been practiced by employing a solvent extraction process on that feed followed by extractive distillation and stripping steps to separately recover the solvent and an aromatic extract (concentrate). The extract was then subjected to one or more distillation steps to separate there from one or more individual aromatic products as ultimate (final) products of the overall process.

In simplest terms, in a solvent extraction process, a feed material containing, for example, benzene mixed with at least one non-aromatic is mixed with a solvent that (i) has a boiling temperature (boiling point) that is quite different from the boiling point of benzene, (ii) preferentially absorbs benzene from the feed, and (iii) naturally physically separates from the undissolved feed. The solvent preferentially absorbs the benzene from the feed. The benzene rich solvent is then subjected to extractive distillation and stripping steps to separate the solvent from the benzene and produce a benzene extract (aromatic extract) from which is recovered a benzene product that is purified of non-aromatics in the feed down to a predetermined maximum non-aromatic weight content (specification). Most, but not all, non-aromatics are physically separated from the aromatics in forming the extract. The remainder of the feed which contains the vast majority, but not all, of the non-aromatics is separately recovered as a raffinate stream for other processing.

The benzene rich aromatic extract contains minor amounts of non-aromatics. The non-aromatic content of the extract often needs to be reduced in order to meet the purity specification set for the benzene product, and all other aromatic products, desired to be produced from this extract. The maximum amount (weight percent, parts per million, etc.) of non-aromatic impurities allowed to be present in a given benzene product is the "predetermined maximum specification" (predetermined specification, maximum specification, or specification). This predetermined specification can vary from process to process and product to product depending on the quality (non-aromatic purification level) desired for a particular benzene product. The purer the aromatic product desired for a given use of that product, the smaller the total non-aromatic content of that product.

Also heretofore, in the practice of the foregoing solvent extraction process, in an attempt to maintain the non-aromatic content of the aromatic products below their predetermined specifications, the aromatic extract was analyzed by conventional gas chromatography to determine the total non-aromatic content of that extract, and process operating changes were made in order to try to maintain the non-aromatic content of the aromatic product below its specification. These operating changes include changes (i) in the feed rate to the solvent extraction step, (ii) the weight ratio of feed to solvent and (iii) the weight ratio of backwash (defined hereinafter) to feed and other process parameters.

However, practice has shown that aromatic solvent exchange processes are notorious for their difficulty in predicting that a desired final aromatic product will meet (be below) its predetermined maximum specification. For example, it is common that the same change in backwash rate to the solvent extractor will not affect the extraction process in the same way every time thereby making it highly unpredictable as to whether such a change will allow the process to meet the specifications for its aromatic products.

As a result of such unpredictability and the rigid specifications, these processes have been heretofore operated in a manner such that their benzene and/or other individual aromatic products have a non-aromatic content that is very far below their predetermined maximum specifications, i.e., lower in non-aromatic content (purer) than necessary to meet the predetermined specifications. That is to say, because of the foregoing unpredictability, the prior art practice has been to make aromatic products that in some cases were unnecessarily pure for the chosen use for those products.

Manufacturing aromatic products that have a non-aromatic content that is far below that which is needed for a desired use of the product reduces the producing capacity of the process and uses more energy to produce a unit of product than would otherwise be used if the process was operated in a manner that produced all its aromatic products closer to their predetermined maximum specifications, i.e., closer to optimal. For example, if a benzene product has a non-aromatic content that is half, 50 weight percent below, its predetermined maximum specification, and it is purer than is necessary for the desired use for that product. This production of a benzene product that is purer than necessary reduces the operating capacity of the process as measured by the amount of feed per unit time that can be introduced to the process, and utilizes more energy in doing so because less product is produced for the same energy expenditure. Thus, producing one or more aromatic products each having substantially less of a non-aromatic content than is required is not optimal operation for the process.

This invention addresses the problem of unpredictability in the operation of such aromatic solvent extraction processes to meet predetermined specifications, and, in so doing, provides a solvent extraction process that not only has greater operational predictability, but also operates more closely to its optimal capacity utilization at minimum energy use.

SUMMARY OF THE INVENTION

In accordance with this invention the aromatic extract is not, as heretofore practiced by the prior art, analyzed for its total non-aromatic content in a single analysis.

Rather, pursuant to this invention, the aromatic extract is analyzed for at least two separate groups of non-aromatics. The first group of non-aromatics have boiling points starting with the lowest boiling non-aromatic and range up to a boiling point near the lowest boiling aromatic product desired from the process, that aromatic product having a predetermined maximum specification as to non-aromatic impurities. The second group of non-aromatics has higher boiling points than the first group of non-aromatics. It is then determined from this analysis what the distribution of lighter and heavier non-aromatics are between the two groups, and how best to adjust the operating parameters of the system to cause the purity of the final aromatic product (or products) to be near its predetermined specification. If determined to be too far below specification, then operating changes are made to move the non-aromatic content in the aromatic product closer to the maximum specification for that product thereby increasing the producing capacity of the system as a whole with optimal energy use per unit volume of aromatic product manufactured. Process parameter changes pursuant to this invention impact the lighter and heavier non-aromatics differently, and by knowing the distribution of the non-aromatics between the two groups analyzed for, optimum operations can be achieved.

DETAILED DESCRIPTION OF THE INVENTION

Figure 1:
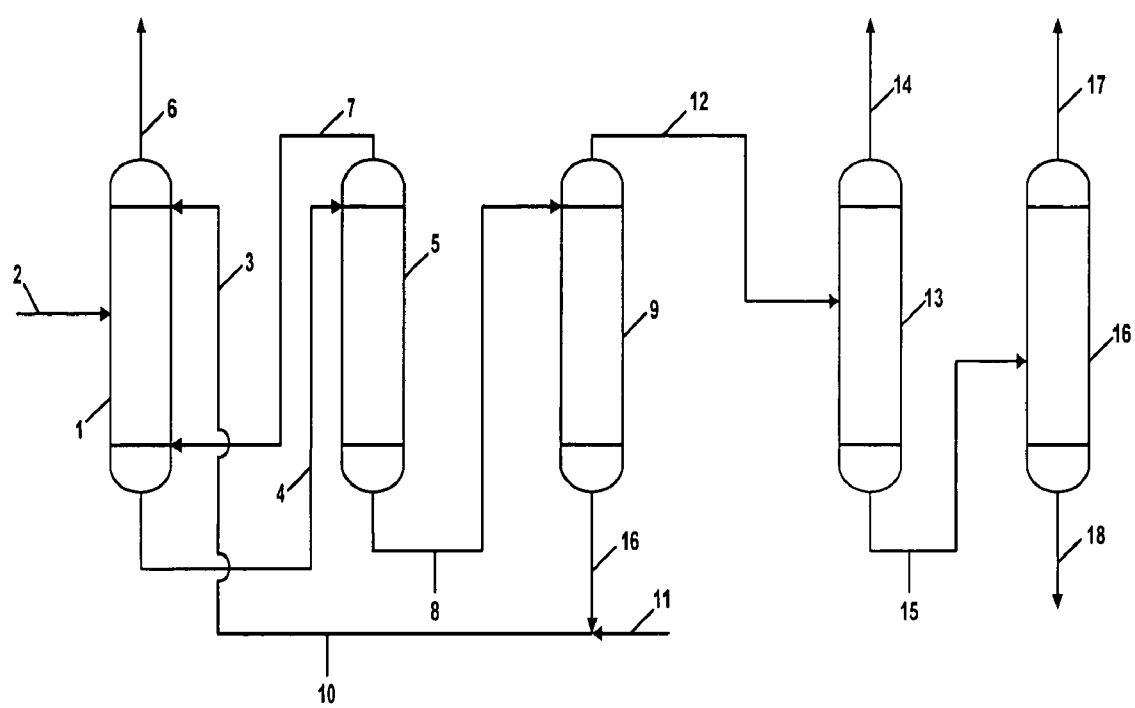
FIG. 1 shows the prior art solvent extraction process referred to here in above.

FIG. 1 shows a typical aromatic solvent extraction system in which a liquid-liquid solvent extractor zone 1 receives incoming process feed 2. Feed 2 can be any mixture of aromatics and non-aromatics, but is typically a catalytic reformate or a hydrotreated pyrolysis gasoline stream from an olefins plant. Generally, feed 2 will contain more than 50 weight percent (wt. %) aromatics and less than 50 wt. % non-aromatics, all based on the total weight of the feed. The aromatics will be in the C6 to C8, inclusive, carbon atom range while the non-aromatics will be in the C5 to C9, inclusive, carbon atom range. The aromatics will include benzene, toluene, xylenes (one or more isomers), ethylbenzene, and the like, while the non-aromatics will be naphthenic and/or paraffinic.

In extractor 1, feed 2 is counter currently contacted with a solvent as described above that will preferentially dissolve aromatics out of feed 2. Suitable solvents are well known, e.g., sulfolane, diethylene glycol, triethylene glycol, tetraethylene glycol, N-methyl pyrrolidone, methyl formamide, and the like. Lean solvent is introduced near the top of extraction zone 1 by way of line 3, and since it is denser than and immiscible with feed 2 it flows downwardly in zone 1 against rising, less dense feed 2. Zone 1 is maintained at an elevated temperature and a pressure sufficiently elevated to maintain the solvent and the feed in the liquid phase. Since the solvent has a solubility selectivity for aromatics over non-aromatics and is immiscible with the feed, aromatics preferentially dissolve in the solvent phase. Non-aromatic rich raffinate 6, less than about 10 wt. % aromatics based on the total weight of the raffinate, is removed overhead for other disposition outside the system shown in the figure.

Hydrocarbon (aromatic and non-aromatic) rich solvent is removed from the bottom of zone 1 by way of line 4, and passed to an extractive distillation zone 5. Zone 5 is operated at elevated temperatures and intermediate pressures to remove the vast majority of non-aromatics and some aromatics, notably benzene, overhead into line 7 for return to the bottom of zone 1 for counter current contact with descending rich solvent. This recycle step is known as backwashing in the art and is important in controlling the composition of the aromatic product or products ultimately recovered from the process. Backwash stream 7 has a lower average boiling temperature (boiling point) than feed 2, and, therefore, the use of stream 7 results in the displacement, from the rich solvent phase in unit 1 into the backwash hydrocarbon phase in unit 1, of the heavier non-aromatic hydrocarbons with an accompanying replacement thereof of lighter non-aromatics into the rich solvent phase in unit 1. This backwash step helps in producing high purity aromatics since it is easier to remove lighter non-aromatics than heavier non-aromatics in zone 5. Stream 7 can contain from about 15 to about 50 wt. %, based on the total weight of the stream, of non-aromatics, notably in the C5 to C8, inclusive, with the remainder aromatics, mostly benzene.

Bottoms 8 of zone 5 is passed to reboiled stripping zone 9 wherein a mixture of aromatics and residual non-aromatics are stripped away from the solvent; the resulting aromatic lean solvent being returned by way of line 10 to near the top of tower 1 for reuse in the solvent extraction step. Fresh, lean solvent is added to the process as needed by way of line 11. Zone 9 is operated at low pressures from slightly superatmospheric to a vacuum under elevated temperatures in order to separate a mixture of aromatics/non-aromatics from the solvent. Zone 9 may be physically separate from zone 5 as shown or may be combined in the same tower shell with unit 5, but the process illustrated will be the same in any case. The hydrocarbon mixture thus separated from the solvent is removed overhead in line 12 and is known as the aromatic extract. Extract 12 is a concentrate rich in aromatics, e.g., containing less than 2 wt. %, sometimes less than 1,500 ppm, non-aromatics. Because of the carefully chosen boiling point for the solvent, stripper 9 readily separates essentially all the aromatics and non-aromatics from the solvent.

Aromatic extract 12 is then subjected to fractionation to remove there from the desired aromatic product or products. FIG. 1 shows a conventional set-up wherein two separate aromatic products are recovered as final products of the process. In this case, extract 12 is passed to a simple distillation tower 13 from which a benzene product 14 is recovered overhead. Benzene stream 14 typically contains less than about 0.5 wt. % non-aromatics based on the total weight of the stream. Bottoms 15 of tower 13 are then passed to another distillation tower wherein a toluene product 17 is recovered overhead. Toluene stream 17 typically contains less than about 5 wt. % non-aromatics based on the total weight of the stream. Bottoms 18 of tower 16 contain mostly C8 and heavier hydrocarbons and are removed from the process for other disposition. If another tower (not shown) was employed on stream 18 to remove at least one xylene isomer and/or ethylbenzene as a product of the process, the C8 aromatic product recovered overhead from this tower would typically contain less than about 1 wt. % of such C8 aromatics based on the total weight of the product.

The foregoing process, as to the production of aromatic products that meet their predetermined specifications, is largely controlled by varying the flow rate amounts of feed 2, backwash 7, and solvent 3. Generally the feed 2 to solvent 3 ratio will be from about 3/1 to about 10/1, and the backwash 7 to feed 2 ratio will be from about 0.3 to about 1.5/1.

The foregoing process, as a whole, is known in the art, see U.S. Pat. Nos. 2,773,918 and 3,361,664, and further detail here is not necessary in order to inform the art.

The operation of an aromatic solvent extraction system (extractor 1, extractive distillation stripper 5, and solvent stripper 9) to form an aromatic extract 12 from which one or more aromatic products 14 and 17 can be obtained is exceedingly complicated to operate. Part of the reason for this is that, relative to each aromatic product recovered from the process, the lighter and heavier non-aromatics in a given feed respond differently to changes in process parameters such as the flow rates of the feed, solvent, and backwash. A single change in one such parameter can cause widely varying results in the process and products thereof. For example, a decrease in the flow rate of backwash 7, typically relative to a benzene product, can have the result of increasing the light non-aromatics in extract 12 and at the same time decreasing the heavy non-aromatics in the same extract 12. Depending on the relative concentration of lighter and heavier non-aromatics in the system, the total non-aromatics in extract 12 may increase or decrease. By analyzing at least two separate groups of non-aromatics, and thereby knowing the relative concentrations of both the lighter and heavier non-aromatics, as opposed to the prior art's single total concentration of non-aromatics, the proper adjustments to operating parameters of the process can be made to allow, pursuant to this invention, for tighter control of the final aromatic product(s) purity.

Although there are a number of changes in process parameters that can affect the composition of the aromatic extract and, hence, the composition of the aromatic products taken from that extract, for sake of clarity and brevity, emphasis herein will be placed on the fact that lighter and heavier non-aromatics in relation to a given aromatic compound do not respond to the same process parameter change in the same manner every time due to other process variables that regularly occur (deliberate, unavoidable, or involuntary) in the operation of an aromatic solvent extraction system.

In the simplest case, such a system can be used to make a single benzene product with a specific predetermined maximum specification. There are, in a normal benzene containing feed material, non-aromatics that are both lower in boiling point (lighter) than benzene and higher in boiling point (heavier) than benzene. These lighter and heavier non-aromatics, as relates to the desired benzene product, respond differently to differing process changes. For example, an increase in backwash flow rate can result in an improvement in the purity of the benzene product by moving non-aromatics out of that product, whereas a decrease in the same backwash can add non-aromatics to the benzene product by adding non-aromatics lighter than benzene thereto, thereby making a less pure aromatic product that is closer to its maximum non-aromatic specification. Similarly, there normally are non-aromatics in solvent extraction feeds that are both lighter and heavier than each of the other aromatics besides benzene that are present in the feed.

Heretofore, the prior art has compositionally analyzed aromatic extract 12 by conventional gas chromatography to determine the total weight of non-aromatics present in that extract. That is to say the prior art sought a single figure that represented the total wt. % of all non-aromatics in the extract. There was no breakdown between the various non-aromatic constituents present, quantitatively or qualitatively. This was due in part to the fact that customers of the various aromatic products looked at a single figure for the total non-aromatics present in an aromatic product when judging whether that product met its predetermined specification or not.

The challenge of making aromatic products to meet specifications while operating the system in an optimum manner is made vastly more complex when, as is the usual case, more than one aromatic product is to be recovered from a single extract. The recovery of a benzene product and a separate toluene product, each having a different predetermined specification, from the same extract, as shown in FIG. 1, is routine. The situation is further complicated when different grades of a given aromatic product are considered. For example, the complexity of processing is increased considerably when the toluene product is required to meet more stringent predetermined specifications, such as nitration or toluene diisocyanate grades.

Yet additional complications stem from multiple aromatic product processes such as the benzene and toluene example of FIG. 1 in that for each separate product the lighter and heavier non-aromatic impurities that tend to stay with the product must be considered. Thus, the operator is concerned about the lighter and heavier non-aromatics that flow with benzene, the lighter and heavier non-aromatics that flow with toluene, and so on, through the entire product slate. From a processing point of view, it is undesirable to have either lighter or heavier non-aromatics dominate in a given aromatic product profile.

Thus, it is a challenge to operate a solvent extraction system so as to produce multiple, separate aromatic products of varying degrees of specification requirements, and to do so without producing some aromatic products that are more pure (contain less non-aromatics) than is necessary to meet the predetermined non-aromatic specifications for those products since making too pure a product sacrifices both the product producing capacity of the system and its energy efficiency.

In accordance with this invention, the total non-aromatic content of an aromatic extract 12 is no longer used to determine process changes. In this invention the system is operated in such a manner that extract 12 is compositionally analyzed for at least two separate and distinct groupings (groups) of non-aromatics, the first group representing the lower boiling non-aromatics present and the second group representing the higher boiling non-aromatics present. This distribution of lighter and heavier non-aromatics, once known, can be used advantageously in predicting the ultimate purity of the individual aromatic product or products of the process. Additional non-aromatic group subdivisions can be analyzed for, if desired, to further help predict the final quality of the aromatic product(s). When a single aromatic product such as benzene is desired, the sole target aromatic compound is benzene, and the first group of non-aromatics analyzed will be those with boiling points ranging from the lowest boiling non-aromatic present to, for example, within about 10° F. of the boiling point of benzene, while the second group of non-aromatics analyzed will include non-aromatics that that are heavier than those found in the first group. Another example is when benzene and toluene are both target aromatic compounds to be produced from the process as separate aromatic products. In such a case, the two non-aromatic groups analyzed for could be a group of non-aromatics that boil close to benzene, and a separate group of non-aromatics that boil close to toluene, the benzene group representing the lighter non-aromatics and the toluene group representing the heavier non-aromatics. Other groupings can be employed such as a group that boils between benzene and toluene, a group that boils close to xylenes, and so on, there being no limit, other than practicality, on the number of separate groups of non-aromatics that the extract could be analyzed for pursuant to this invention. The analyses of the various groupings of non-aromatics can be carried out by conventional gas chromatography as is now practiced by the prior art to determine the total wt. % of non-aromatics in an extract, and, therefore, is well known in the art. The analysis can be carried out on individual physical samples taken from the process or on line in the process.

In the example where benzene is the sole target aromatic compound and the sole aromatic product of the process, the relative amounts of the lighter and heavier non-aromatics can be balanced, by adjustment of extraction unit operating parameters in known manner, to provide for the highest possible system capacity, and tight control of product quality. This is possible because the different operating parameters, such as backwash flow rate and solvent flow rate impact the two groups of non-aromatics differently. By knowing the distribution of the non-aromatics between the two (or more) separate groups analyzed for, the operator can determine how best to adjust the individual parameters to produce a final aromatic product that is closer to its predetermined specification. When, in the prior art method, only the single, total non-aromatic concentration in extract 12 is measured, no information is provided as to which operating parameter needs to be adjusted. The prior art approach thus leads to certain of the stream flows and/or temperatures in the system being operated in a way that consumes more system capacity than if the operating parameters were adjusted to the more efficient settings. Because the single total non-aromatics measurement does not give good insight into the proper parameter adjustments, various aromatic products typically are produced with purities greater than required by their predetermined specifications. By subdividing the total non-aromatics in accordance with this invention, and thereby providing for more data on the actual non-aromatic distribution, more information is obtained as to the proper setting of the various system operating parameters. Thus, by this invention, the operators of the system can predictably control the aromatic product quality closer to the predetermined specification. The movement of non-aromatics in a product toward its predetermined maximum specification is demonstrated in FIG. 2.

Figure 2:
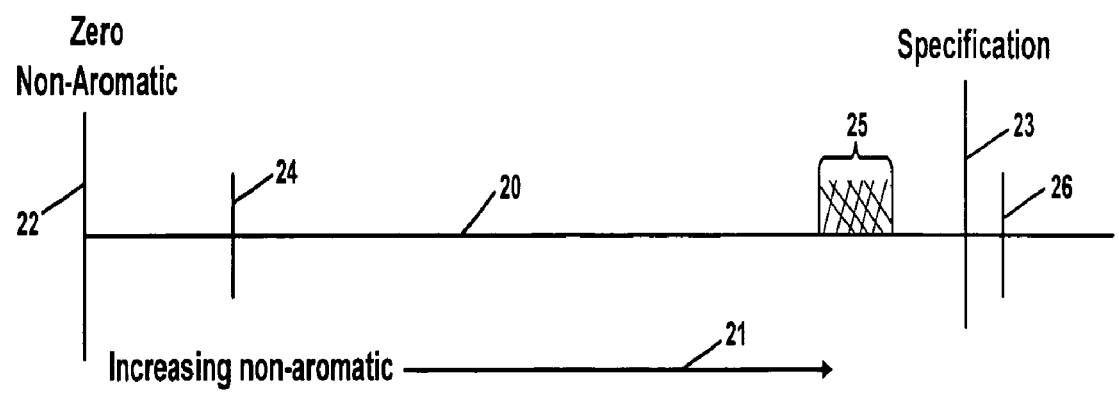
FIG. 2 demonstrates the movement of non-aromatic impurities into an aromatic product in order to move that product toward its predetermined maximum specification pursuant to this invention.

FIG. 2 represents graphically the results of the foregoing two group compositional analysis and comparison process for a specific extract 12 from which a single benzene product is to be obtained. Horizontal line 20 in this figure represents the amount of non-aromatics that will be in the benzene product if no process changes are made, with the amount of non-aromatic increasing to the right as shown by arrow 21. Line 22 represents pure benzene with no (zero) non-aromatic content. Line 23 represents the predetermined maximum specification for total aromatics in the benzene product. Line 24 represents what the non-aromatic content of the benzene product will be if no process changes are made. Line 24 is about 80 wt. % less than the maximum specification 23. Thus, if nothing is done, the process, as it is currently working, will make too pure a benzene product in relation to what is tolerated by specification 23.

Pursuant to this invention, in response to the analysis results represented by FIG. 2, one or more process parameters for the process are changed by the operator in known manner so that the non-aromatic content of the benzene product will move closer to its specification 23, e.g., into the wt. % range 25. For example, a typical benzene product can have a maximum specification 23 for total non-aromatics in the final benzene product of 1,000 parts per million (ppm). If the two group analyses of this invention show that the total non-aromatic content 24 of the benzene product will be 400 ppm if the process is not changed, then the operator can take steps to change one or more process parameters such as the backwash rate so that the non-aromatic content of the product is increased to 800 ppm thereby producing a product that more closely approaches the maximum specification 23 of 1,000 ppm. In this manner, more non-aromatics will be moved into the benzene product without exceeding maximum specification 23. At the same time, again based on the two group analyses of this invention, the lighter to heavier non-aromatic profile, as it relates to the benzene product, can be modified by the operator as desired. Should too much non-aromatic be added to the product and the total non-aromatic content of the product reach point 26, then the product will exceed its maximum specification and will not be marketable. This invention puts increased, but allowable, amounts of non-aromatics into the product and thereby increases the capacity of the system as a whole in turn allowing for an increased rate for feed 2 and better utilization of the overall capacity of the system. This increased throughput is achieved without an increase in energy expenditure so that an increase in product volume is achieved without increasing the energy used to achieve the greater product output. In this manner the solvent extraction system is operated so that each aromatic product desired predictably has a composition closer to its predetermined maximum specification.

Often, in the operation of a solvent extraction process, particularly when more than one product was produced, one or more products were unknowingly made that were unnecessarily pure thus penalizing the productivity of the system. By this invention, an operator can determine whether any products are too pure and the system not running optimally, and can take steps to change the operating conditions to correct the matter. This can be done for each product of the system thereby leveraging the production capacity improvements achieved by this invention.

How far away from specification 23 towards zero non-aromatics 22 is too far, will vary widely depending on the process and its product slate, but generally, when the actual non-aromatic content 24 is more than about 50 wt. % (based on the total weight of non-aromatics between the specification 23 and zero non-aromatics 22) less than maximum specification 23, it is time to make some changes that will move the actual non-aromatic content of the aromatic product towards specification 23, above the 50 wt. % mark, and into range 25.

As an example, when benzene is the sole target aromatic compound and, therefore, benzene is the sole product of the process, the first group of non-aromatic impurities analyzed for will be the lighter boiling group. The scope of this group can vary widely, but its upper (maximum) boiling limit will generally be in the range of from about 10° F. below the boiling point of benzene to about 10° F. above that boiling point. The second group of non-aromatic impurities analyzed for will be the heavier boiling group i.e., non-aromatics that boil in a range that is heavier than the first group. The analysis for this second group is necessary to obtain information about the distribution between lighter and heavier non-aromatics. Information as to the relative amounts of lighter and heavier non-aromatics gives a much improved guide on how to change process parameters to produce a product (or products) that is closer to its predetermined specification without exceeding that specification.

If a second target aromatic compound, e.g., toluene, is to be recovered from the same extract as the benzene above, then the second group analysis would be of non-aromatics that boil heavier than benzene. The range for this second, toluene, group can also vary widely, but its upper boiling point will generally be from about 25° F. below the boiling point of toluene up to about 25° above that boiling point. For xylene and any of its isomers individually and for ethylbenzene the group boiling range can vary widely as well, but its upper boiling limit will generally be from about 10° F. below the boiling point of the material in question to about 10° F. above that boiling point.

It can be seen from the foregoing that this invention provides a means, heretofore not available to operators, for balancing the non-aromatic impurities between the various aromatic products to allow for the maximum allowable non-aromatics in each aromatic product. This invention also allows an operator to balance the relative amounts of lighter and heavier non-aromatics in each product as desired to achieve a desired, specific profile. All of these results in a system that operates at a higher capacity while meeting the predetermined specifications for all products, even though, with a higher feed rate to the solvent extractor 1, and more non-aromatics than ever are introduced into the process.

EXAMPLE

In a process where benzene is the sole target aromatic compound, the feed to the solvent extraction unit is a hydrotreated pyrolysis gasoline containing benzene, other aromatics, and naphthenic and paraffinic hydrocarbons in the C5 to C9, inclusive, carbon atom range. This feed, at a flow rate of about 10,000 barrels (42 gallon) per day (BPD) is counter currently contacted in extractor 1 with tetraethylene glycol, which performs as a selective solvent for extracting the aromatics from the feed, at a temperature of about 160° F. and a pressure of about 120 pounds per square inch gauge (psig). The solvent is introduced near the top of unit 6 at a rate of about 60,000 BPD.

An overhead stream 6 is taken from extractor 1 which contains 99 wt. %, based on the total weight of the stream, of non-aromatics, the remainder being essentially aromatics.

The hydrocarbon rich solvent 4 removed from the bottom of extractor 1 is passed to an extractive distillation tower 5 which is operated at about 250° F. at a pressure of about 20 psig, and wherein a backwash overhead is formed that contains about 30 wt %, based on the total weight of the stream, non-aromatics, with the remainder being aromatics, predominantly benzene. This backwash stream, at a rate of 10,000 BPD, is returned to near the bottom of solvent extraction unit 1.

The bottoms 8 of unit 5 contains primarily solvent and aromatics along with less than about 0.1 wt. %, based on the total weight of the stream, of non-aromatics, and is passed to a reboiled stripper 9 operated at a temperature of about 270° F. and a pressure of about 20 psig to thermally strip the solvent of hydrocarbons and form an overhead aromatic rich extract 12 that contains about 99.9 wt. %, based on the total weight of the stream, aromatics, with the remainder being non-aromatics. This stream includes aromatics that are both lighter and heavier than benzene. The bottoms 16 of unit 9 contain essentially only solvent that is free of hydrocarbons, and is returned to near the top of the solvent extraction unit 1 for reuse in preferentially extracting aromatics from feed material that contains both aromatics and non-aromatics.

Extract 12 is compositionally analyzed by gas chromatography as to two separate groups of non-aromatics. The first group is lighter non-aromatics that have a boiling point ranging from the lowest boiling non-aromatic present up to about the boiling point of benzene. The second group of non-aromatics has higher boiling points than the first group. From the results of the gas chromatographic analysis of these two groups it is seen that the benzene product which the process will produce, if no process changes are made, will contain 200 ppm total non-aromatics. Since the predetermined maximum specification for this benzene product is 1,000 ppm, this product is far purer as to benzene than is required. Based on this knowledge, the process operator will change the backwash rate from 10,000 BPD to 8,000 BPD, increase the solvent ratio from 6:1 to 6.5:1, and increase the feed rate from 10,000 BPD to 11,000 BPD in order to incorporate more total non-aromatics into the benzene product of the process so that the total non-aromatic content of that product increases from the 200 ppm level to the 800 ppm level. The light non-aromatics will also increase, but the heavier non-aromatics will decrease or change little (with the increased feed rate). This allows for the recovery of an increased amount of extract 12 from unit 9 which allows for an increased input of feed to extraction unit 1 with less energy consumed per barrel of extract 12.

We claim:

1. In a method for recovering at least one target aromatic compound from a mixture of aromatic and non-aromatic compounds using a solvent extraction system process under operating parameters such that a solvent is employed to absorb said aromatics and produce an aromatic extract that contains primarily aromatics with minor amounts of non-aromatic impurities, said target aromatic compound being subsequently separated by distillation from said aromatic extract to form a first aromatic product that contains primarily said target aromatic compound and minor amounts of said non-aromatic impurities, said non-aromatic impurities being required to be present in said first aromatic product in amounts less than a predetermined maximum specification, the improvement comprising compositionally analyzing said aromatic extract to determine at least two separate groups of lighter and heavier boiling non-aromatics, the first group of said at least two separate groups having lighter boiling points that start with the lowest boiling point non-aromatic present in said extract, the second group of said at least two separate groups having non-aromatic boiling points higher than said first group, determining the distribution of lighter and heavier non-aromatics between said at least two groups, and adjusting said operating parameters so that said first aromatic product has a non-aromatic impurity content that is nearer to its predetermined maximum specification.

2. The method of claim 1 wherein said first group of non-aromatic impurities has a maximum boiling limit that is within at least about 25° F. of the boiling point of said target aromatic compound, and said amount of non-aromatic impurities present in said first aromatic product before said adjusting of said operating parameters is at least about 50 weight % less than said predetermined maximum specification.

3. The method of claim 1 wherein said target aromatic compound is benzene, and said first group has an upper boiling limit that is in the range of from about 10° F. below the boiling point of benzene up to about 10° F. above the boiling point of benzene.

4. The method of claim 3 wherein there is a second target aromatic compound to be produced as a second aromatic product, said second group of said two separate groups has non-aromatics that are present in said aromatic extract and are higher boiling than said first group, determining the distribution of lighter and heavier non-aromatics between said two separate groups, and changing said operating parameters so that said second aromatic product has a non-aromatic impurity content that is closer to its predetermined maximum specification for said second aromatic product.

5. The method of claim 4 wherein said second target aromatic compound is toluene, said second group of non-aromatic impurities has an upper boiling limit in the range of from about 25° F. less than the boiling point of toluene up to about 25° F. more than the boiling point of toluene, and said amount of non-aromatic impurities present in said second aromatic product before changing said operating parameters is at least about 50 wt. % less than said predetermined specification for said second product.

6. The method of claim 4 wherein said aromatic extract is additionally compositionally analyzed for at least one additional group of non-aromatic impurities that are present in said aromatic extract.

7. The method of claim 6 wherein said at least one additional target aromatic compound is selected from the group consisting of at least one xylene and ethyl benzene.

8. The method of claim 7 wherein one of said at least one additional group of non-aromatic impurities has an upper boiling limit in the range of from about 10° F. less than the boiling point of the target aromatic compound in question up to about 10° F. more than such boiling point, and said amount of non-aromatic impurities present in said at least one additional aromatic product before changing said operating parameters is at least about 50 wt. % less than the predetermined specification for said target aromatic compound in question.

* * * * *